US009211102B2

(12) United States Patent
Taskinen et al.

(10) Patent No.: US 9,211,102 B2
(45) Date of Patent: Dec. 15, 2015

(54) IMAGE PLATE TEMPLATE FOR KEEPING AT LEAST ONE IMAGE PLATE USED IN MEDICAL IMAGING IN ORDER WITH RELATION TO AN IMAGING OBJECT

(71) Applicant: PaloDEx Group Oy, Tuusula (FI)

(72) Inventors: Jari Taskinen, Tuusula (FI); Timo Klemola, Kerava (FI); Kaapo Paulanto, Nurmijärvi (FI); Mika Anttila, Espoo (FI); Petri Hyypia, Helsinki (FI); Jorma Honkala, Kauniainen (FI)

(73) Assignee: PaloDEx Group Oy, Tuusula (FI)

( * ) Notice: Subject to any disclaimer, the term of this patent is extended or adjusted under 35 U.S.C. 154(b) by 71 days.

(21) Appl. No.: 13/926,535

(22) Filed: Jun. 25, 2013

(65) Prior Publication Data

US 2014/0161235 A1 Jun. 12, 2014

(30) Foreign Application Priority Data

Jun. 27, 2012 (FI) .................................. 20125734

(51) Int. Cl.
*A61B 6/00* (2006.01)
*A61B 6/14* (2006.01)

(52) U.S. Cl.
CPC . *A61B 6/463* (2013.01); *A61B 6/14* (2013.01); *A61B 6/4494* (2013.01); *A61B 6/467* (2013.01); *A61B 6/547* (2013.01); *A61B 6/56* (2013.01)

(58) Field of Classification Search
CPC .............. A61B 6/00; A61B 6/14; A61B 6/44; A61B 6/56; A61B 6/463; A61B 6/467; A61B 6/4233; A61B 6/4494; A61B 6/547; G03B 42/02; G06F 19/321

USPC ........... 378/98, 165, 169, 172, 174, 189, 191, 378/210; 250/580, 582, 583, 584; 340/5.66, 340/10.42, 10.52
See application file for complete search history.

(56) References Cited

U.S. PATENT DOCUMENTS

| | | | |
|---|---|---|---|
| 2005/0213702 A1* | 9/2005 | Akagi | 378/37 |
| 2006/0239521 A1 | 10/2006 | Crucs | |
| 2006/0261296 A1* | 11/2006 | Heath et al. | 250/580 |
| 2010/0171052 A1* | 7/2010 | Thoms | 250/584 |

FOREIGN PATENT DOCUMENTS

| | | |
|---|---|---|
| EP | 2 386 904 A1 | 11/2011 |
| WO | 2010109064 A1 | 9/2010 |

OTHER PUBLICATIONS

Finnish Search Report for priority application FI 20125734, dated Apr. 9, 2013.

* cited by examiner

*Primary Examiner* — Irakli Kiknadze
*Assistant Examiner* — Julio M Duarte-Carvajalino
(74) *Attorney, Agent, or Firm* — Andrus Intellectual Property Law, LLP (57) ABSTRACT

The invention relates to an image plate template for keeping at least one image plate used in medical imaging in order with relation to an imaging object. The template comprising at least receiving means for receiving the at least one image plate and displaying means for displaying information in order to associate a patient with the at least one image plate. The template may also comprise communication means for communicating information from said image plate to an external device for displaying information in order to associate a patient with the at least one image plate.

18 Claims, 5 Drawing Sheets

IMAGE PLATE TEMPLATE FOR KEEPING AT LEAST ONE IMAGE PLATE USED IN MEDICAL IMAGING IN ORDER WITH RELATION TO AN IMAGING OBJECT

CROSS-REFERENCE TO RELATED APPLICATIONS

This application claims priority of Finnish Patent Application No. 20125734, filed Jun. 27, 2012, which application is incorporated herein by reference.

TECHNICAL FIELD

The application relates generally to an image plate template for keeping at least one image plate used in medical imaging in order with relation to an imaging object.

BACKGROUND

In modern medical imaging, images of objects are taken on image plates and image information is read from the plates by a reading device. One image plate can typically be used several times and the image information is reset between imaging operations. Thus, many different persons will use a certain image plate during its life span and it will contain images of several patients and even different body parts of different patients.

Used image plates may become mixed up since image information read from an image plate may end up to a wrong doctor or it may become associated with a wrong patient or, in a case of series of image plates where a mutual order of the plates is important, the plates may get into a wrong order so that treatments, which are meant to be directed to certain parts of a patient, are directed to wrong parts. In some circumstances the image information of an image plate cannot later be associated with the correct patient.

A known solution for this problem is to set used image plates on a magnetic full mouth series (FMS) template having places for e.g. 18 or 20 image plates. In e.g. intraoral imaging the places on the template form arcs that correspond with arc of upper and lower jaws. Image plates containing an image taken from each position of the arcs are attached magnetically on a place that correspond with a position in the upper or lower jaw, whereupon it is possible to keep the plates in predefined places. Later on a staff can conclude by means of the place that from which position of the upper or lower jaw the image in the image plate has been taken.

SUMMARY

One object of the invention is to provide a fast and simple method for associating image plates having images of a patient used in medical imaging with the patient so that this connection lasts safely during a workflow of the images.

One object of the invention is fulfilled by providing an image plate template of claim 1, a method of claim 11, and a computer program of claim 12.

According to an embodiment of the invention an image plate template for keeping at least one image plate used in medical imaging in order with relation to an imaging object comprises at least receiving means for receiving the at least one image plate and displaying means for displaying information in order to associate a patient with the at least one image plate.

The term "image plate template" refers to a template that is used for managing image plates and image information in the plates and, thereby, controlling a medical imaging operation. The template may comprise a place for at least one image plate and e.g. in intraoral imaging, an individual place for each plate used in the imaging of teeth.

The term "image plate" refers to reusable or disposable image plates used in medical imaging, e.g. in intraoral imaging. The plate is preferably shielded inside a protecting means, e.g. a protective pouch, during radiography, whereupon an X-ray image is captured by placing an object to be imaged, e.g. a patient or part of the patient, between an X-ray source and the plate covered by the protecting means. Alternatively, it can be used plates, which are cleanable e.g. by autoclaving, when the shielding is not utilized.

According to an embodiment of the invention a method for keeping at least one image plate used in medical imaging in order with relation to an imaging object in an image plate template comprises at least receiving information at least through a wired and/or wireless connection from a workstation computer running an imaging software and/or an image plate reader, and/or through a docking station interface of the template from a docking station of the template comprising a user interface, and/or from a user interface of the template, and/or through a radio frequency connection from at least one of the computer, a patient card, an electronic identity card, handheld device, and a mobile phone, and displaying the received information.

The term "wired connection" refers to e.g. an USB (Universal Serial Bus) connection, Ethernet connection or any other connection that transmits signals through wires, fibers or any other solid medium.

The term "wireless connection" refers to e.g. a short range radio wireless communication, e.g. a Bluetooth, Wi-Fi, and Wireless USB (WUSB) connection. The wireless connection refers also to other wireless communication.

The term "workstation computer" refers to e.g. a personal computer, mobile phone, handheld device (e.g. PDA or smart phone), tablet, or any other computer used for processing image plates.

According to an embodiment of the invention a computer program for keeping at least one image plate used in medical imaging in order with relation to an imaging object in an image plate template, when the computer program is run in a computer, comprises at least receiving code for receiving information through a wired and/or wireless connection from a workstation computer running an imaging software and/or an image plate reader, and/or through a docking station interface of the template from a docking station of the template comprising a user interface, and/or from a user interface of the template, and/or through a radio frequency connection from at least one of the computer, a patient card, an electronic identity card, handheld device, and a mobile phone, and displaying code for displaying the received information.

Further embodiments of the invention are defined in dependent claims.

An image plate template according to embodiments of the invention improves patient name tracking when the template holds and informs a user for a patient identification, i.e. whose images are on the template.

An image plate template according to embodiments of the invention enables to synchronize a patient name with images since the template can automatically send the patient name forward to e.g. an image plate reader or an imaging software so that the patient name can be attached to each image.

An image plate template according to embodiments of the invention can offer easily radiation information during a workflow of an imaging process since the information displayed by the template is clearly available, e.g. image plate usage related information of whether the plate is radiated or not can be provided e.g. when the image plate comprises this information and the template and the plate can communicate with each other.

The verb "to comprise" is used in this document as an open limitation that neither excludes nor requires the existence of also unrecited features. The verbs "to include" and "to have/has" are defined as to comprise.

The terms "a", "an" and "at least one", as used herein, are defined as one or more than one and the term "plurality" is defined as two or more than two.

The term "another", as used herein, is defined as at least a second or more.

The term "or" is generally employed in its sense comprising "and/or" unless the content clearly dictates otherwise.

For the above-mentioned defined verbs and terms, these definitions shall be applied, unless a different definition is given in the claims or elsewhere in this description/specification.

BRIEF DESCRIPTION OF THE FIGURES

The exemplary embodiments of the invention will be described with reference to the accompanying figures, in which.

DETAILED DESCRIPTION OF THE FIGURES

Figure 1:
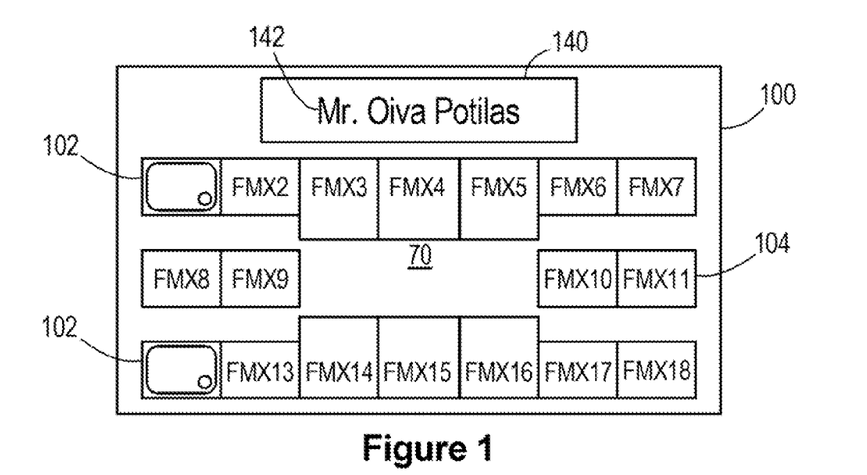
FIG. 1 illustrates a layout of a first image plate template.

FIG. 1 illustrates a first image plate template 100 for keeping at least one image plate 102 used in medical imaging, as well as information in the plate 102, in order with relation to an imaging object that relates to a patient.

The template 100 that is a FMS template comprises receiving means 104 for receiving the plates 102 and displaying means 140 for displaying information 142 that comprises e.g. at least one of the following: a patient's name, patient's identity number, room number of a patient, examination room, or doctor, number of workstation computer, doctor's name, and requested image information. The information 142 comprising the patient's name in the figure is used to keep the plates 102 and the patient tracked, i.e. to associate the patient with one plate 102 that is attached on the template 100. The plates 102 can be attached on the template 100 with transferring and/or protecting means (not shown).

The plates 102 can be inserted in an image plate reader within the transferring means so that they are conveyed and read in the reader. The transferring means may be an imaging plate tray, adapter, cassette, or image plate autoloader.

The protecting means is used for shielding a plate 102 during an imaging process so that an X-ray image is provided by placing the object between an X-ray source and the plate 102 enveloped within the protecting means. The protecting means may become in touch with the patient and patient's liquids during the imaging process, e.g. an intraoral imaging, whereupon the plate 102 is protected by the protecting means when it is inserted in a patient's mouth. The protecting means may be e.g. a protective pouch having a liquidproof structure.

The template 100 comprises magnetic material that enables to attach the plates 102, or other suitable means, having at least one material that is attracted by the magnetic template 100, on the receiving means 104 or some other place on the template 100. Alternatively, the template 100 may comprise e.g. a thin metal surface that is utilized for attaching the plates 102 having at least one magnetic material that attracts the thin metal surface. It is also possible, if the 102 is placed inside the transferring and/or protecting means, that the transferring and/or protecting means comprise at least one material that is attracted by the magnetic template 100 or, alternatively, when the template comprises the thin metal surface, the transferring and/or protecting means comprise at least one magnetic material that attracts the thin metal surface. Alternatively, pouches or slots can also be used as a receiving means 104 so that the plates 102 can be attached on the template 100 without a magnetic feature. The protecting means can also be used together with the pouches or slots.

The receiving means 104 may comprise at least one predefined marked place 104 on the template 100 for at least one plate 102, whereupon the place 104 determines an anatomical location of the image in the plate 102. So. e.g. in intraoral FMS imaging, there is an individual place 104 marked as FMX1-FMX18 for each plate 102 used in the imaging of teeth. The template 100 in the figure comprises places 104 for upper and lower teeth, front teeth, and posterior teeth. Two plates 102 have been attached on places FMX1 and FMX12. Alternatively, if the template 100 is a bitewing (BW) template, it will comprise preferably 2 or 4 image plate places, e.g. FMX8-FMX11. Respectively, if it is used the pouches or slots, those are arranged on the template 100 similarly as the marked places 104.

The displaying means 140 comprise a reusable information field to where a user can write the necessary information 142 e.g. by pen or any other suitable means and/or from where it can be erased or removed so that the template 100 is ready for a next imaging operation. Alternatively, the user can utilized self-adhesive layers to which the necessary information 142 has been written for attaching the information 142 on the template 100. The self-adhesive layers are naturally easy to remove so that the innominated template 100 can be reused. Alternatively, the displaying means 140 can be provided by a pad of sticky notes that has been attached on the template 100, whereupon a used note can be removed easily when the information in it is not valid anymore.

Figure 2A:
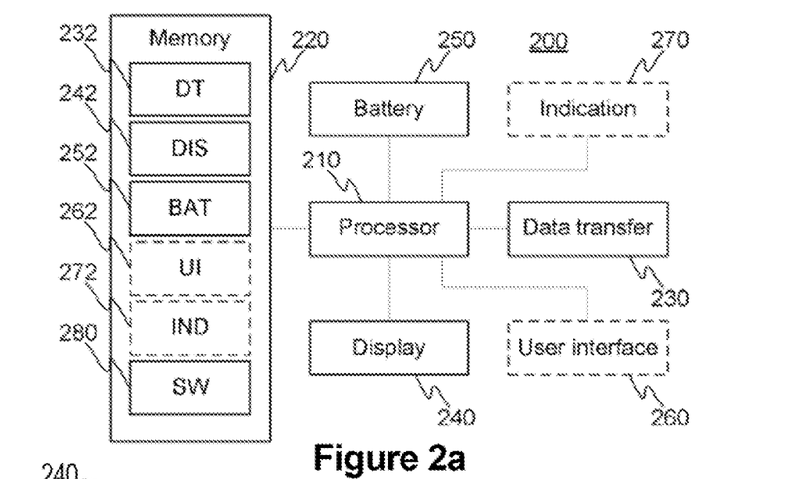
FIG. 2a-2b illustrate functional elements and a layout of a second image plate template.

FIG. 2a illustrates a second image plate template 200 for keeping image plates and information in the plates in order with relation to an imaging object.

The template 200 comprises similar receiving means as the template 100 in FIG. 1, at least one processor 210 for performing user and/or software initiated instructions and for processing data, and at least one memory 220 for storing and maintaining data, e.g. instructions, softwares, and data files. The template 200 also comprises a data transfer unit 230 for sending and/or receiving data through a wired and/or wireless communication network, an integrated display unit 240 for displaying information, and a battery unit 250 as a power source that can be charged through a charging interface (not shown) or replaced by a new battery. Alternatively, the template 200 can comprise a power cable or other source of energy, or an interface for the cable so that it can be connected to an external power source by means of the cable.

In addition, the template 200 may comprise a user interface unit 260 for inputting data and instructions. The user interface 260 comprising at least one of followings: a keyboard, loudspeaker system, touchpad, touchscreen, mouse, voice control unit for receiving voice commands, e.g. at least one microphone, gesture control unit for receiving gesture commands, e.g. at least one camera, or orientation control unit for detecting an orientation or motion of the template 200, e.g. at least one acceleration sensor or any other orientation sensor. The template 200 may comprise indication means 270, e.g. LEDs in a near vicinity of marked places or several LEDs in each marked place or its boundaries for lightning the place or changing its colour, for indicating an exposed image plate or, alternatively, unexposed plates. Each place have at least one dedicated indication means 270. The identification of the exposed or unexposed plates can be provided by a pressure sensors or other suitable sensors belonging to the indication means 270 that recognize when the plates are set on the places and taken away from the places. The template 200 recognizes when e.g. an unexposed plate is set on the place for a first time, whereupon, when the unexposed plate to be exposed is taken away for setting it in a patient's mouth, it start to light the place since it recognizes that the plate is set on it. Alternatively, if used plates are "smart" image plates capable of storing also other information than image information, e.g. information concerning whether it has been exposed or not, and capable of communicating wirelessly with other devices, e.g. with the template 200, the recognition process can be provided so that the template 200 provides the indication when it receives the information that a plate has been exposed from that particular plate. The template 200 may also comprise a docking station interface (not shown) through which the template 200 can be connected to a docking station (not shown). The docking station can comprise its own user interface for inputting data and instructions.

The at least one memory 220 comprises at least data transfer application 232 for controlling the data transfer unit 230, display application 242 for controlling the display unit 240, a battery application 252 for controlling the battery unit 250 and possibly its charging, and a computer program code 280 for controlling a process for associating a patient with image plates.

The at least one memory 220 may comprise also a user interface application 262 for controlling the user interface 260 and an indication application 272 for controlling indication means 270. In addition, The at least one memory 220 may comprise a docking station application for controlling a docking station interface.

The at least one memory 220 and the computer program code 280 are configured to, with the at least one processor 210, cause the template 200 to receive information that comprises e.g. at least one of the following: a patient's name, patient's identity number, room number of a patient, examination room, or doctor, number of workstation computer, doctor's name, and requested image information. The information is received by means of a data transfer unit 230 through a wired connection, e.g. a USB or Ethernet, and/or wireless connection, e.g. a WLAN connection, and the information is from a workstation computer, e.g. a personal computer, from a mobile phone, or from a handheld device, e.g. PDA or tablet, that runs an imaging software. The information can also be from an X-ray device, image plate reader, docking station comprising the user interface, or user interface 260 of the template 200. The template 200 is also caused to display the received information by a display 240 that can be e.g. a LCD (liquid crystal display), LED (light emitting diode), or OLED (organic LED) display. Alternatively, the display 240 can be e.g. a touchscreen comprising means for inputting information into the template 200.

In addition, the template 200 may be caused to send the received information or other information, e.g. control information relating to imaging parameters, by the data transfer unit 230 to at least one of the computer, X-ray device, and image plate reader when the template 200 establishes the wired and/or wireless connection to those and/or when the user establishes a sending command through at least one of the user interfaces 260. The control information is used in order to control at least one of the computer, X-ray device, and reader.

The computer program 280 in the memory 220 is configured to keep at least one image plate in order with relation to an imaging object in the template 200. It comprises receiving code for receiving information by a data transfer unit 230 through a wired and/or wireless connection from a workstation computer running an imaging software and/or an image plate reader, and/or through the docking station interface from the docking station that comprises the user interface for entering the information, and/or from the user interface 260, and/or through a radio frequency connection from at least one of the computer, a patient card, an electronic identity card, handheld device, and a mobile phone. The computer program 280 also comprises displaying code for displaying the received information.

The computer program 280 can further comprise sending code for sending the received information or other information, e.g. control information relating to imaging parameters, by the data transfer unit 230 to at least one of the computer, X-ray device, and the image plate reader when the template 200 establishes a wired and/or wireless connection to those and/or when the user establishes a sending command through at least one of the user interfaces 260.

The computer program 280 can further comprise receiving code for receiving at least one user input through the user interface unit 260 configured to receive user inputs. The user interface 260 comprises at least one of the followings: a keyboard, touchpad, touchscreen, mouse, voice control unit, gesture control unit, and orientation control unit.

The computer program 280 can further be a computer program product comprising a computer-readable medium bearing computer program code embodied therein for use with a computer.

Figure 2B:
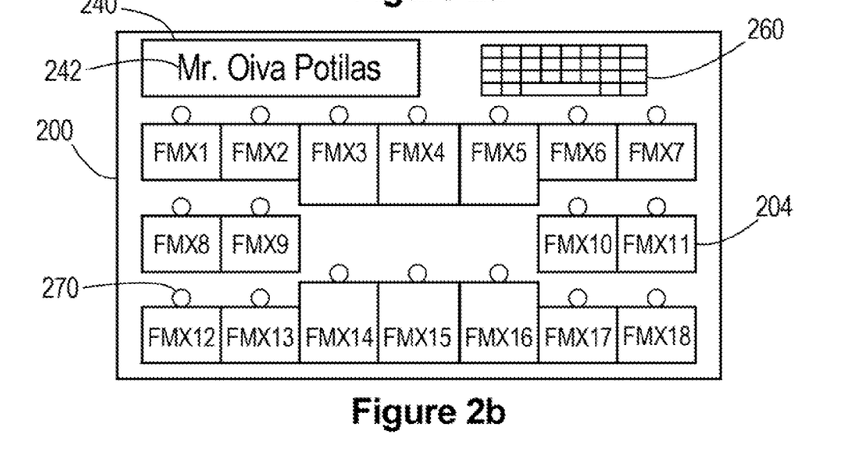

FIG. 2b illustrates a layout of a second image plate template 200, where it comprises marked places 204 for receiving image plates, a LCD unit 240 for displaying information 242, e.g. a patient's name, a keyboard 260 for inputting the displayed information 242, and LEDs 270 of each place 204 for indicating exposed image plates. The display 240 can display the information in a format, which comprises e.g. at least one of the followings: text format, barcode format, and figure format. A layout of the templates 100, 200 can be changeable according to personal or clinical preferences.

Figure 3:
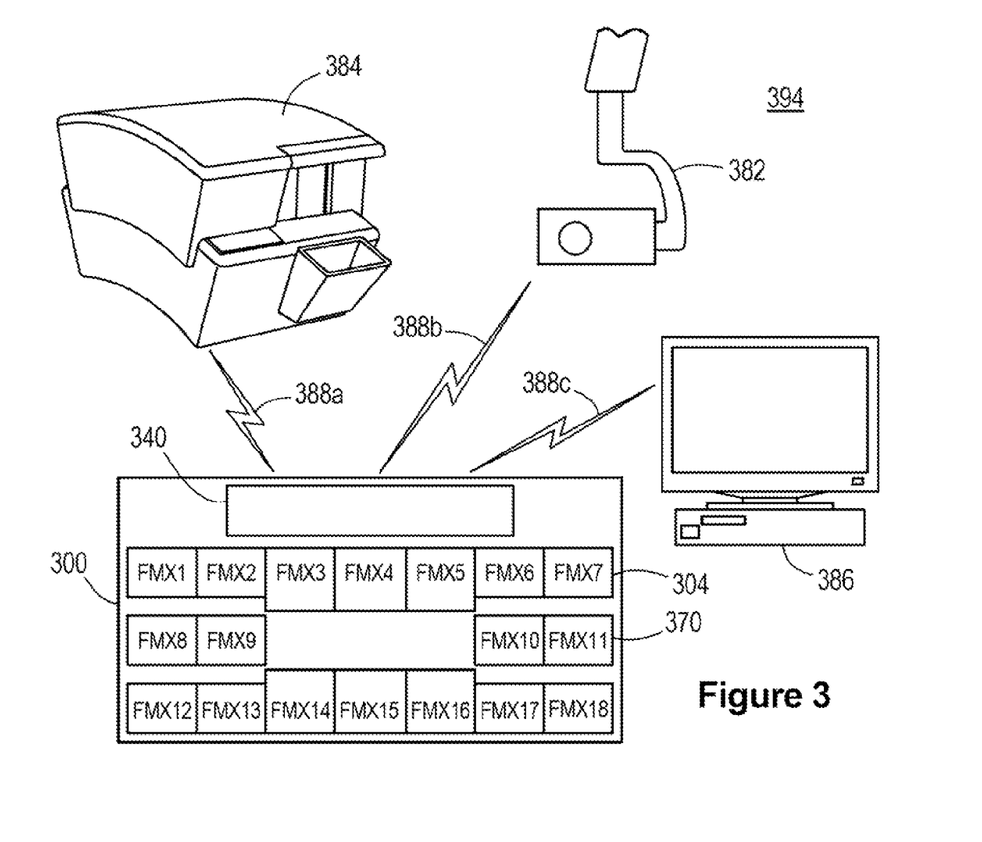
FIG. 3 illustrates an imaging system that utilizes the second image plate template.

FIG. 3 illustrates an arrangement 394, where a FMS template 300 is used for keeping images plates (not shown) in their correct position and connecting the plates to a certain position and a patient. The template 300 comprises places 304 for the plates, which has indication means 370 that provides the indication by means of markings of the places 304 that change colour. The template 300 also comprises a LCD display 340 for displaying information.

The arrangement 394 also comprises an X-ray device 382 for providing images on the plates, an image plate reader 384 for reading and erasing the plates, and a workstation computer 386 for running an imaging software that is used for capturing, viewing, printing, and storing images. The template 300 can be connected with at least one of the X-ray device 382, reader 384, and workstation 386 by a wireless and/or wired connections 388a, 388b, 388c so that it is possible to transfer information, e.g. identification information, image information, and control information, between devices 300, 382, 384, 386. Naturally, even if it not shown in the figure, information can also be transferred between other devices 382, 384, 386 through the connections 388a, 388b, 388c, e.g. between the reader 384 and the workstation 386, and between the workstation 386 and the X-ray devices 382 when needed.

The information transfer between the devices 300, 382, 384, 386 can still be utilized even if it is used an imaging sensor (not shown) as a an image receptor instead of the plates.

Figure 4:
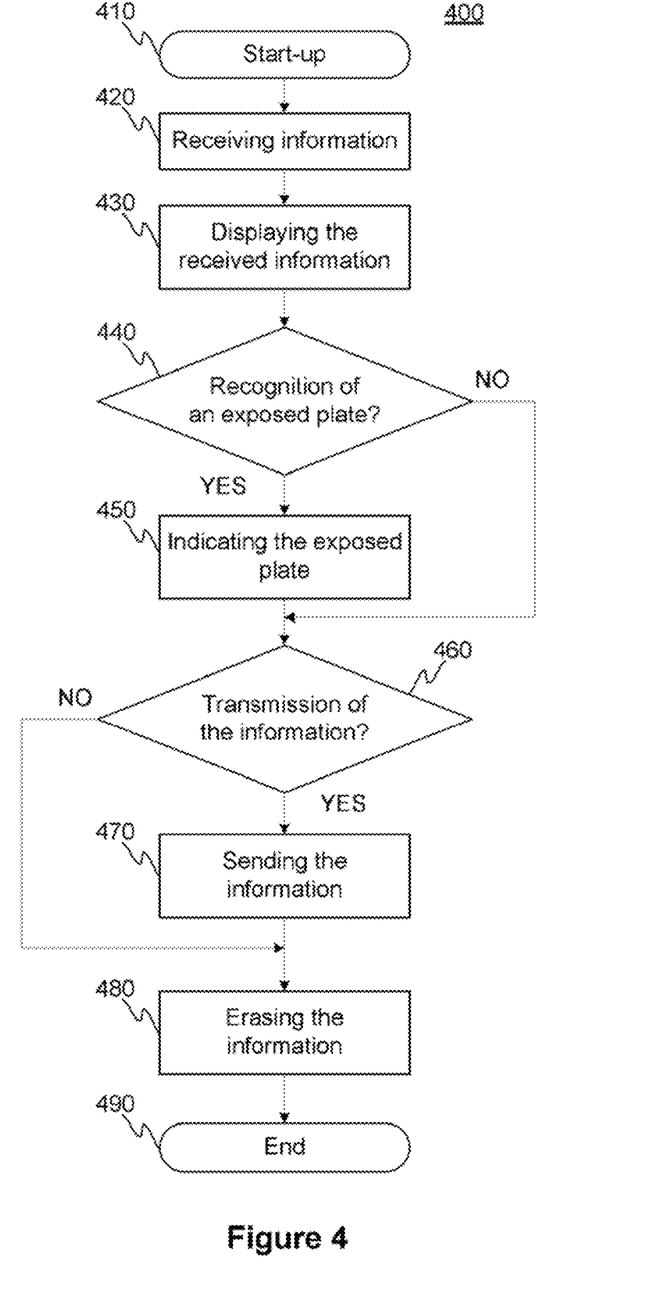
FIG. 4 illustrates a flowchart of a method for keeping image plates in order with relation to an imaging object in the second image plate template.

FIG. 4 illustrates a method 400 for keeping at least one image plate used in medical imaging, e.g. intraoral imaging, in order with relation to an imaging object in e.g. an image plate template according to FIGS. 1, 2a, 2b.

During a method start-up in step 410, e.g. a magnetic FMS template having a display and being adapted to keep the image plates in an anatomical order is started and necessary actions, e.g. initializations and software updates, are performed. Respectively, an image plate reader that is adapted to read image plates, an X-ray device adapted to provide an image of an object on the image plates, a workstation computer adapted to run an imaging software, and a docking station of the template can be started if necessary.

Then, e.g. before imaging of a patient, the staff attaches unexposed image plates used in the imaging on marked places of the template. The template comprises magnetic material that enables to attach one or more plate, or other suitable means, comprising at least one material that is attracted by the magnetic template. The marked places on the template determine an anatomical location of an image in a plate.

In step 420 a data transfer unit of the template receives information, which can be e.g. a patient's name. The information can be received through a wired and/or wireless connection from the workstation computer, image plate reader, or X-ray device. Alternatively, it can be received through a connection interface between the template and docking station when a user enters the information by means of a user interface. e.g. a keyboard or touchscreen, of the docking station. Alternatively, the information can come from a user interface of the template when the user enters it and such exists, or through an USB interface of the template from a memory device, e.g. a memory stick. Alternatively, the information is possible to receive through a radio frequency connection from the workstation computer, a patient card, an electronic identity card, handheld device, e.g. a smart phone or tablet computer, a mobile phone, or image plate capable of storing at least the information and image information, and capable of communicating wirelessly with other devices, e.g. with the template.

In step 430 the received information is displayed by the display of the template and possibly stored in a memory of the template, whereupon the plates on the template are assigned to a patient whose name was received earlier.

Then, the image plates are taken from the template one at a time and an image is provided to each plate by means of the X-ray device from a location in a patient's mouth that corresponds with the location on the template. After the image has been provided on the plate, it is returned its own location, i.e. the marked place, on the template, whereupon a user can conclude based on the location of the attached plate, without reading the plate by the image plate reader, from which anatomical location the image has been taken.

If the template comprises in step 440 indication means for each image plate place in order to indicate an exposed or, alternatively, unexposed plates and it is capable of recognizing when an image plate is exposed, it provides an indication after recognizing that an unexposed plate is taken away from the place or the exposed plate is returned on its place in step 450.

After all necessary images has been taken, the exposed image plates can be read by means of the image plate reader so that the exposed plates are taken one at a time from the template and put into the reader that reads the plates and then preferably erases the read plates before ejecting them. The ejected plates having no image information are ready for next imaging after certain preparion phases.

When in step 460 the template is configured to receive information, which starts a sending operation, or a sending command, and then to send the displayed information, i.e. the patient's name, to e.g. the workstation or reader, it sends in step 470 the information by the data transfer unit to the workstation and/or the reader through the wired and/or wireless connection e.g. automatically after the template recognizes when all plates have been read and/or when the user establishes a sending command through at least one of the user interfaces. The interface that receives the user's command can be e.g. a user interface of the template, docking station, workstation, reader, or X-ray device. Naturally, if there is no physical connection between the template and the used user interface like the template's user interface or docking station's user interface when it is physically connected to the template, the user's command is received through the wired and/or wireless connection.

Then, in step 480, after the sending operation has been completed, or if the template lacks such operation, the displayed information is erased from the display and possibly from the memory when it is stored in the template. The erasing operation is provided e.g. automatically after the information has been sent or after receiving an erasing command from the user through the user interface, the template receives a new information to be displayed, or the template is turned off, or after the template has received a erasing command through at least one of the user interfaces that can be e.g. the user interface of the template, docking station, workstation, reader, or X-ray device. Naturally, if there is no physical connection between the template and the used user interface, the user's command is received through the wired and/or wireless connection. If the erased information is kept in the memory, it can be retrieved from the memory when necessary.

Then, in step 490, the method 400 ends.

Figure 5A:
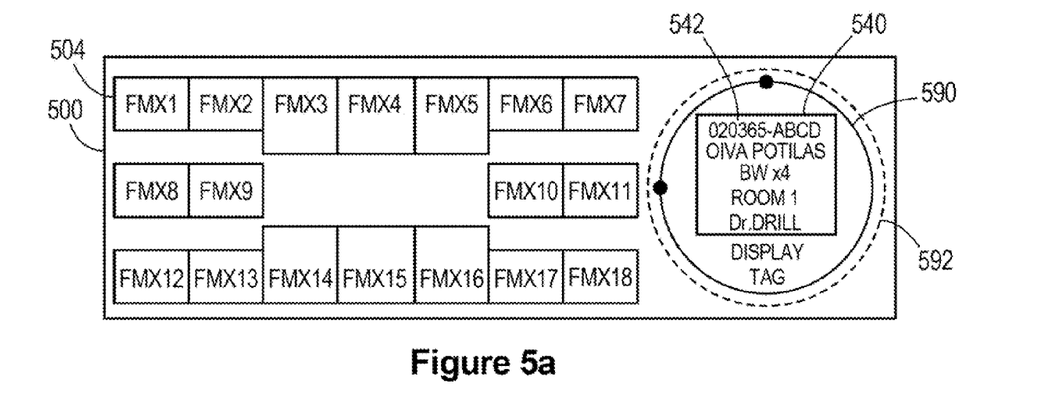
FIG. 5a-5c illustrate a layout of a third image plate template with a display tag, functional elements of the display tag, and its alternative layout.

FIG. 5a illustrates a layout of a third image plate template 500 for keeping image plates and information therein in order with relation to an imaging object, which template 500 is similar as the template 100 in FIG. 1 except displaying means 590. The template 500 comprises marked receiving means 504 for the plates and displaying means 590, e.g. a wireless display tag, that comprises a display unit 540 for displaying information 542. The information 542 may comprise e.g. at least one of the following: a patient's name, patient's identity number, room number of a patient, examination room, or doctor, number of workstation computer, doctor's name, and requested image information. The tag 590 has been attached on a marked place 592 dedicated to it and it displays a patient's identity number, name, image information (BW×4), examination room, and doctor's name in the figure. Alternatively, the wireless display tag 590 can be a modile device, e.g. a mobile phone, tablet computer, personal digital assistant (PDA), or other hand held device that comprises the display unit 540 for displaying the information 542. Alternatively, the template 500 may lack the place 592 that is dedicated to the tag 590, whereupon the tag 590 is maintained e.g. in a pocket of a staff person, from where it can communicate with other devices capable of wireless communication when a staff person, as well as the tag 590, arrives in a vicinity of such device.

Figure 5B:
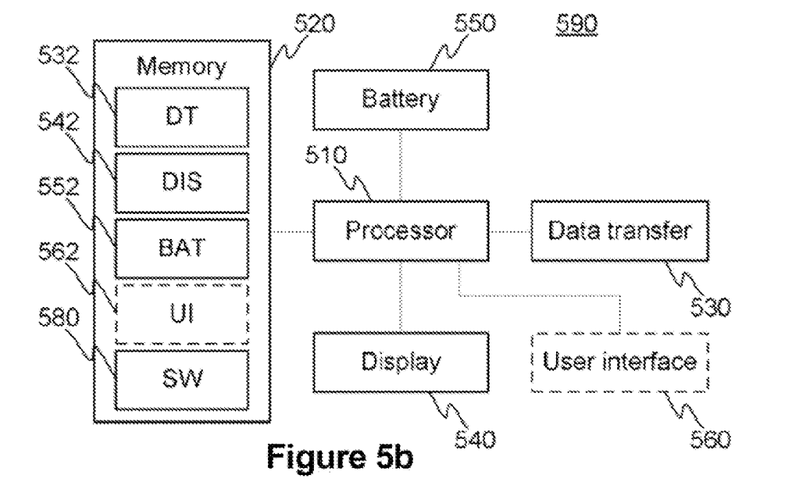

FIG. 5b illustrates functional elements of the displaying means 590, e.g. a RF identification (RFID) tag, that can be attached on the template 500 at least one processor 510 for performing user and/or software initiated instructions and for processing data, and at least one memory 520 for storing and maintaining data, e.g. instructions, softwares, and data files. The tag 590 also comprises a data transfer unit 530 for sending and/or receiving data through e.g. a wireless short range radio frequency (RF) communication, an alphanumeric and/or graphical display unit 540 for displaying information, and a rechargeable battery unit 550 that can be charged through a contactless near field battery charging. Alternatively, the tag 590 can be charged by means of a battery charger, whereupon the tag 590 comprises an interface (not shown) for the charger.

The at least one memory 520 comprises at least data transfer application 532 for controlling the data transfer unit 530, display application 542 for controlling the display unit 540, a battery application 552 for controlling the battery unit 550 and possibly its charging, and a computer program code 580 for controlling a process for associating a patient with image plates.

If the template 500 is a "smart" template having a processor, memory, and data transfer unit as FIG. 2a-2b describes and the display tag 590 is a mobile phone or handheld device, the display tag may be configured to communicate with the template 500, the image plate reader, or the X-ray device for transferring information comprising the information and/or control information, e.g. imaging parameters or other control information, to those in order to keep the plates in order and to control directly at least one of the template 500, reader, and X-ray device. It is also possible that the reader and/or X-ray device can be controlled indirectly through the template 500 by the display tag 590, or by means of the template 500 after receiving the information or control information from the display tag 590.

The computer program 580 may further comprise displaying code for displaying the information by the tag 590 that comprises the display 540, the memory 520, and the data transfer unit 530 for transferring data wirelessly through the RF connection. The tag 590 also comprises attaching means, e.g. material that is attracted by a magnetic material, adhesive layer, or clip, so that it can be attached on the template 500. Alternatively, it is possible that the tag 590 does not have any attaching means, whereupon it can be carried e.g. in a pocket of a staff person.

In addition, the computer program 580 may comprise sending code for sending the information wirelessly through the RF connection to the image plate reader and/or the computer.

In addition, the computer program 580 may comprise, when the template 500 has a processor, memory, and data transfer unit and the display tag 590 is a mobile phone or handheld device, sending code for sending to the template 500, the image plate reader, or the X-ray device the information and/or control information, e.g. imaging parameters or other control information in order to keep the plates in order and/or to control directly at least one of the template 500, reader, and X-ray device.

In addition, the computer program 580 may further comprise indicating code for indicating an exposed image plate in the at least one marked place 504.

The computer program 580 may be a computer program product comprising a computer-readable medium bearing computer program code embodied therein for use with a computer.

The tag 590 can receive the information 542 wirelessly from at least one of the workstation computer, a patient card, an electronic identity card, handheld device, e.g. PDA or tablet, and a mobile phone, and/or to send the information 542 wirelessly to the image plate reader and/or the workstation computer.

Figure 5C:
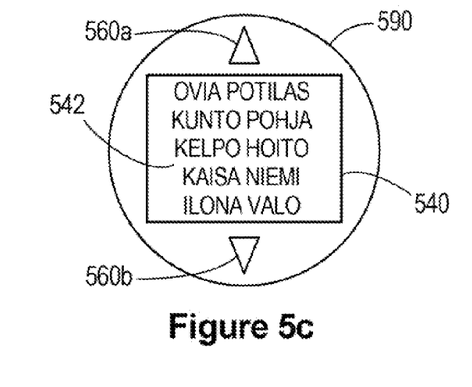

FIG. 5c illustrates another tag 590 that is used together with the template 500 for keeping image plates and information therein in order with relation to an imaging object.

The tag 590 is similar as the tag in the previous FIGS. 5a, 5b but it also comprises a user interface unit 560 for inputting data and instructions. The user interface 560 comprising at least one of followings: a touch screen 540, touch buttons 560a, 560b, and at least one sensor (not shown), e.g. at least one accelerations sensor, for detecting tilting and/or moving of the tag 590. Thus, the at least one memory 520 comprises also a user interface application 562 for controlling the user interface 560.

When the user interface 560 comprises the buttons 560a, 560b, a user selects a displayed patient by scrolling a patient list 542 by means of the up button 560a and/or down button 560b, or by means of e.g. tilting the tag 590 in directions of the buttons 560a. 560b. When a correct name is e.g. in the middle of the display 540 and the user does not scroll the list 542 for a while, e.g. 2-5 seconds, the display 540 displays information relating to the selected patient. Alternatively, if the user interface 560 also comprises the touchscreen, the user may select the patient by touching the patient's name on the list 542. The displayed information may comprise e.g. a patient's identity number, name, image information, examination room, and doctor's name similarly as in the previous figure.

Figure 6:
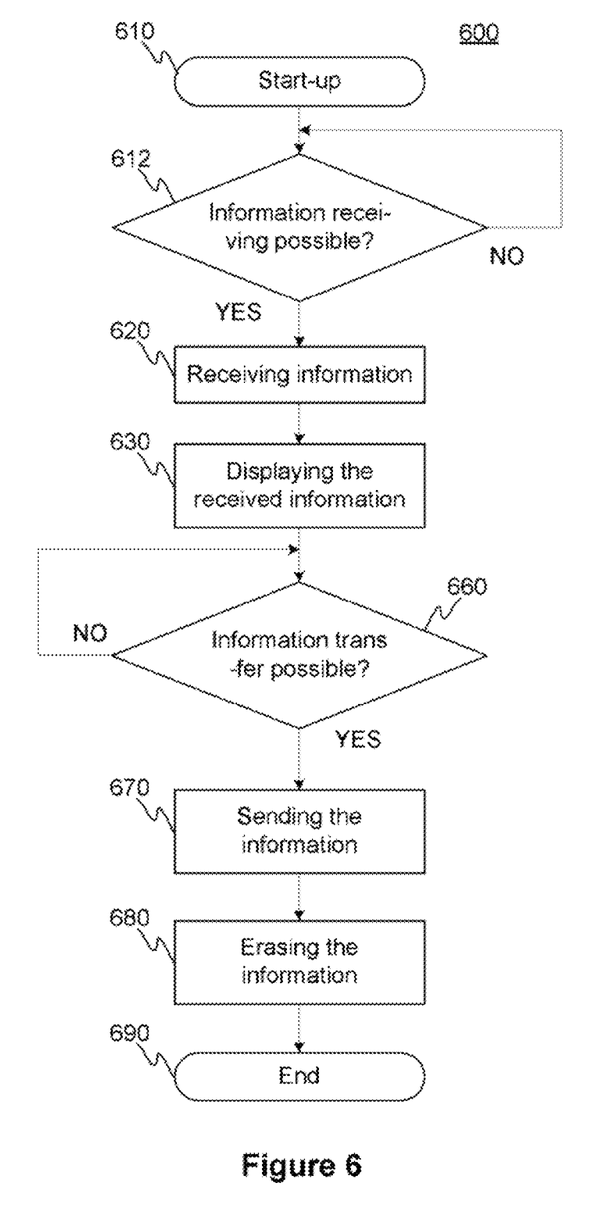
FIG. 6 illustrates a flowchart of a method for keeping image plates in order with relation to an imaging object in the third image plate template with the display tag.

FIG. 6 illustrates a method 600 for keeping at least one image plate used in medical imaging, e.g. intraoral imaging, in order with relation to an imaging object in/on e.g. an image plate template according to FIG. 5a by means of a display tag according to FIGS. 5a, 5b, 5c. The display tag comprises an alphanumeric or a graphical display, a memory, and a data transfer unit for transferring data wirelessly through the RF connection. It can also comprise attaching means, e.g. a material that is attracted by a magnetic material, adhesive layer, or dip, so that it can be attached on the template, but not necessarily. The template can also be a "smart" template that is similar to the template described in FIGS. 2a-2b and that is connectable to a docking station, whereupon it is possible to provide through the template and/or docking station an information transfer from the tag to other devices capable of communicating.

In this example the template is a magnetic BW template having 4 marked places that determine an anatomical location of an image in the plate. The template comprises magnetic material that enables to attach one or more plate, the display tag, or other suitable means, comprising at least one material that is attracted by the magnetic template.

During a method start-up in step 610, an image plate reader, an X-ray device, a workstation computer, and the display tag, e.g. a tag or a mobile phone, which are capable of communicating with each other by a wireless connection, e.g. short range RF or infrared (IR) connection, or wired connection, e.g. a USB or Ethernet connection, are started and necessary actions, e.g. initializations and software updates, are performed.

The tag can receive imaging related information, e.g. a patient's identity number, patient's name, room number, workstation number, doctor's name, requested images etc. when the tag is in proximity of or in contact with a RFID unit (transceiver) that is capable of transmitting and/or receiving information through RF connection, and possibly capable of providing contactless recharging of a battery of the tag, and that is in a wired, e.g. USB, or wireless connection with the workstation storing the information or that is integrated into the workstation. Alternatively, the information can be received from an electronic identity card, e.g. a patient's identity card, or a mobile device, e.g. a mobile phone or tablet computer, storing the information, i.e. "the electronic identity card", in its memory. So, when it is possible to provide the information transfer in step 612, a data transfer unit of the tag receives the information in step 620.

The received information is stored in the memory of the tag and in step 630 it is displayed by the display. Tags can be used to read one imaging and/or patient related information per tag, whereupon the tags form a physical "worklist" or alternatively, if the tags can store multiple patients, i.e. imaging and/or patient related information, in queue, it creates an electronic worklist in the memory and a staff can select a patient and his/her information to be displayed and used by scrolling the list.

When a desired information is displayed, the tag and required amount of unexposed image plates to be used in the imaging are attached on the template by means of magnetism, whereupon the plates on the template are assigned to a patient whose name is displayed by the attached tag. This way the staff can verify the patient throughout the imaging operation. The plates can be "addressed" to be auto-populated to e.g. the template of the imaging software run by the workstation based on their order in the template. Naturally, the plates can be attached earlier on the template, e.g. during steps 610, 612, 620, 630.

Then, the unexposed plates are taken from the template one at a time and an image is provided to each plate by means of the X-ray device from a location in a patient's mouth that corresponds with the location on the template. After the image has been provided on the plate, it is returned its own location on the template, whereupon the staff can conclude based on the location of the plate, without reading the plate by the reader, from which anatomical location the image has been taken.

If the template is capable of indicating an exposed or, alternatively, unexposed plates and it is capable of recognizing when a plate has been exposed, it can provide the indication. In the case of "smart" image plates and template, which can communicate with each other, the indication is provided similarly as it is described in context of FIG. 2a.

After all necessary images has been taken, the tag, which is attached on the template or unfastened from it, is taken in proximity of or in contact with a RFID unit (transceiver) that is capable of transmitting and/or receiving information through RF connection, and possibly capable of providing contactless recharging of a battery of the tag, and that is in a wired, e.g. USB, or wireless connection with the reader or that is integrated into the reader. Thus, when it is possible to provide the information transfer from the tag to the reader or its external RFID unit in step 660, a data transfer unit of the tag sends the information in step 670 through the RF connection to the reader or its external RFID unit.

The exposed plates is read by the reader so that the exposed plates are taken one at a time from the template and put into the reader that reads the plate and then erases it before ejecting. The ejected plates having no image information are ready for next imaging after certain preparation phases, e.g. a disinfection of the plates when the plates are reusable plates.

During the reading operation of the plates the imaging and/or patient related information received by the reader or its external RFID unit are paired with the images by tagging the information to the images, which are addressed to the correct workstation and patient on the basis of the information read from the tag.

The images can be read in same order as addressed when they were attached on the template, whereupon the images are auto-populated to the imaging software in the workstation that is connected with the reader by a wired, e.g. Ethernet, or wireless connection.

When the tag comprises the electronic worklist with multiple patients, the staff selects a correct imaging and/or patient information to be displayed before the tag is taken near the reader or its external RFID unit reading the information. Then, the selection is provided before the X-ray imaging.

The reader or its external RFID can send a read receipt or other messages to the tag after the information transfer in step 670 so that the tag can store it in connection with the said displayed patient.

In step 680, after the reader or its external RFID unit has read the information in the tag, the displayed information is erased from the display and possibly from the memory. The erasing operation can be provided e.g. automatically after the information transfer has been completed. If the erased information and possibly the message associated with it is kept in the memory, it (those) can be retrieved from the memory when necessary.

Then, in step 690, the method 600 ends.

Figure 7:
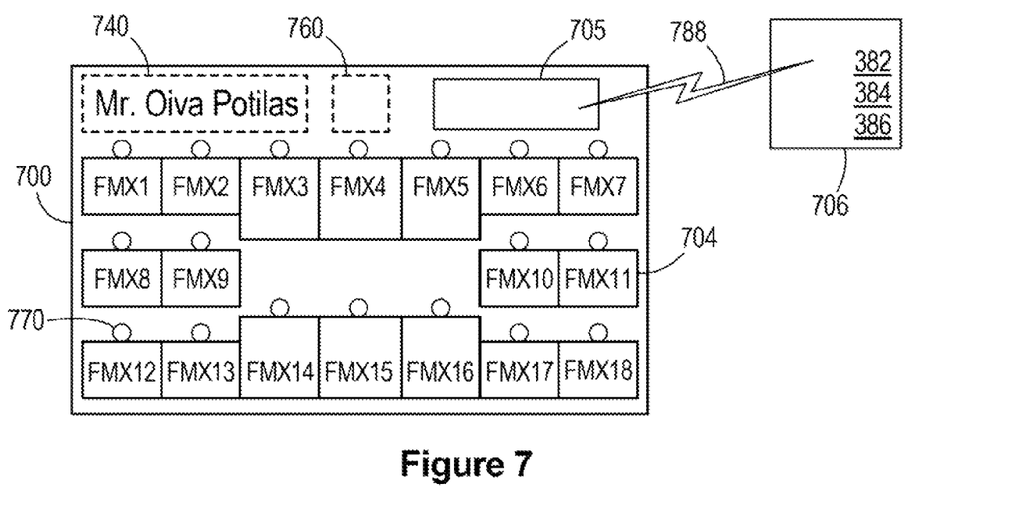
FIG. 7 illustrates an example of a layout of another image plate template.

FIG. 7 illustrates an example of a layout of another image plate template 700 for keeping at least one image plate used in medical imaging in order with relation to an imaging object, wherein the template comprises at least receiving means 704 for receiving the at least one image plate. In addition said image plate template 700 comprises also communication means 705 for reading information 788 from said image plate and sending the information 788 to an external device 706 for displaying information in order to associate a patient with the at least one image plate.

The external device 706 advantageously comprises the display tag, which can be e.g. a mobile phone, tablet computer, handheld device or any other device or mobile device comprising the display for displaying the information, the memory, and the data transfer unit for transferring data via a wired and/or wireless connection 788.

The template 700 may be configured to send the information to the computer, the X-ray device, and/or the image plate reader or other external device 706 via said communication means 705, 788 when the template establishes the wired and/or wireless connection 788 to those and/or when the user establishes a sending command through at least one of the user interfaces. The template may optionally comprises a user interface unit 760.

The image plate template 700 may, according to another embodiment, also comprise marked places 704 for receiving image plates, and optionally also an integrated display unit 740 for displaying information. In addition the template 700 may also comprise indication means 770, e.g. LEDs in a near vicinity of marked places or several LEDs in each marked place or its boundaries for lightning the place or changing its colour, for indicating an exposed image plate or, alternatively, unexposed plates.

It is to be noted that the communication means 705 can be, for example a transmitter, receiver, transceiver, and/or RFID reader, and may be implemented in a wired or wireless way, such as by RFID technique or Bluetooth, for example.

The invention has been now explained above with reference to the aforesaid exemplary embodiments and the several advantages of the invention have been demonstrated. It is clear that the invention is not only restricted to these embodiments, but comprises all possible embodiments within the spirit and scope of the invention thought and the following claims.

The invention claimed is:

1. An image plate template for keeping a plurality of image plates used in medical imaging in order with relation to an imaging object, the image plate template comprising:
   receiving means for receiving the plurality of image plates; and
   displaying means for displaying information in order to associate a patient with the plurality of image plates; and
   at least one indication means for indicating an exposed image plate;
   wherein the receiving means comprises at least one marked place on the template that determines an anatomical location of an image of an image plate of the plurality of image plates received at the at least one marked place, each marked place having at least one indication means.

2. The template of claim 1, further comprising magnetic material that enables to attach the at least one image plate on the template when the at least one image plate comprises at least one material that is attracted by the magnetic material, the receiving means comprise at least one marked place on the template that determines an anatomical location of an image of the at least one image plate.

3. The template of claim 2, further comprising at least one processor and at least one memory comprising a computer program code, the at least one memory and the computer program code is configured to, with the at least one processor, cause the template to perform at least receiving the information from at least a workstation computer running an imaging software, X-ray device, and/or an image plate reader, from a docking station comprising a user interface, and/or from a user interface of the template, and displaying the received information.

4. The template of claim 1, where the displaying means comprises an information field, where a user can write the information and/or erase it.

5. The template of claim 1, further comprising at least one processor and at least one memory comprising a computer program code, the at least one memory and the computer program code is configured to, with the at least one processor, cause the template to perform at least receiving the information from at least a workstation computer running an imaging software, X-ray device, and/or an image plate reader, from a docking station comprising a user interface, and/or from a user interface of the template, and displaying the received information.

6. The template of claim 5 wherein the template is caused to perform sending the information to the computer, the X-ray device, and/or the image plate reader when the template establishes the wired and/or wireless connection to those and/or when the user establishes a sending command through at least one of the user interfaces.

7. The template of claim 6 wherein the template is caused to perform receiving at least one user input through a user interface unit, the user interface unit comprising at least one of the followings: a keyboard, touchpad, touchscreen, mouse, voice control unit, gesture control unit, and orientation control unit.

8. The template of claim 5 wherein the template is caused to perform receiving at least one user input through a user interface unit, the user interface unit comprising at least one of the followings: a keyboard, touchpad, touchscreen, mouse, voice control unit, gesture control unit, and orientation control unit.

9. The template of claim 1, where the displaying means comprises a display tag that comprises a display for displaying the information, a memory, and a data transfer unit for transferring data wirelessly, the tag comprises attaching means so that it can be attached on the template.

10. The template of claim 9 where the tag is configured to receive the information wirelessly from at least one of the computer, a patient card, an electronic identity card, handheld device, and a mobile phone, and/or to send the information wirelessly to the image plate reader and/or the computer.

11. The template of claim 1, where the displaying means comprises the display tag that is a mobile phone, tablet computer, handheld device or any other mobile device comprising the display for displaying the information, the memory, and the data transfer unit for transferring data wirelessly, the display tag being configured to communicate with the template, the image plate reader, or the X-ray device for transferring information comprising the information and/or control information to the template, the image plate reader, or the X-ray device.

12. The template of claim 11 where the tag is configured to receive the information wirelessly from at least one of the computer, a patient card, an electronic identity card, handheld device, and a mobile phone, and/or to send the information wirelessly to the image plate reader and/or the computer.

13. An image plate template for keeping at least one image plate used in medical imaging in order with relation to an imaging object, the template comprising:
   receiving means for receiving the at least one image plate;
   communication means for reading and sending information from said image plate to an external device for displaying information in order to associate a patient with the at least one image plate; and
   at least one indication means for indicating an exposed image plate;
   wherein the receiving means comprises at least one marked place on the template that determines an anatomical location of an image of an image plate of the plurality of image plates received at the at least one marked place, each marked place having at least one indication means.

14. The template of claim 13 further comprising magnetic material that enables to attach the at least one image plate on the template when the at least one image plate comprises at least one material that is attracted by the magnetic material, the receiving means comprise at least one marked place on the template that determines an anatomical location of an image of the at least one image plate.

15. The template of claim 13 wherein the template is caused to perform sending the information to the computer, the X-ray device, and/or the image plate reader via said communication means when the template establishes the wired and/or wireless connection to those and/or when the user establishes a sending command through at least one of the user interfaces.

16. The template of claim 13 where the external device comprises the display tag that is a mobile phone, tablet computer, handheld device or any other device or mobile device comprising the display for displaying the information, the memory, and the data transfer unit for transferring data via a wired and/or wireless connection, the display tag being configured to communicate with the template, the image plate reader, or the X-ray device for transferring information comprising the information and/or control information to the template, the image plate reader, or the X-ray device.

17. A method for keeping at least one image plate used in medical imaging in order with relation to an imaging object in an image plate template, the method comprising at least:

receiving at least one image plate at one of a plurality of marked places on the image plate template, each of the marked places associated with a portion of the imaging object;

receiving information at least through a wired and/or wireless connection from a workstation computer running an imaging software, X-ray device, and/or an image plate reader, and/or through a docking station interface of the template from a docking station of the template comprising a user interface, and/or from a user interface of the template, and/or through a radio frequency connection from at least one of the computer, a patient card, an electronic identity card, handheld device, and a mobile phone, and displaying the received information.

18. A non-transient computer readable medium encoded with a computer program configured for keeping a plurality of image plates used in medical imaging in order with relation to an imaging object in an image plate template, the computer program comprising at least, additionally configured for:

receiving at least one image plate at one of a plurality of marked places on the image plate template, each of the marked places associated with a portion of the imaging object; and receiving information at least through a wired and/or wireless connection from a workstation computer running an imaging software, X-ray device, and/or an image plate reader, and/or through a docking station interface of the template from a docking station of the template comprising a user interface, and/or from a user interface of the template, and/or through a radio frequency connection from at least one of the computer, a patient card, an electronic identity card, handheld device, and a mobile phone, and displaying the received information, when run in a computer.

* * * * *